US000001899H

United States Statutory Invention Registration [19]

[11] Reg. Number: H1,899

Bhat et al. [45] Published: Oct. 3, 2000

[54] DIAGNOSTIC USES OF IGFBP-2

[75] Inventors: Ratan Bhat, West Chester; Matthew S. Miller, Newtown; Patricia C. Contreras, West Chester, all of Pa.

[73] Assignee: Cephalon, Inc., West Chester, Pa.

[21] Appl. No.: 08/827,894

[22] Filed: Aug. 22, 1996

[51] Int. Cl.[7] ..... A01N 37/18

[52] U.S. Cl. ..... 514/2; 514/12; 530/399

[58] Field of Search ..... 514/2, 12; 530/399

[56] References Cited

U.S. PATENT DOCUMENTS 5,128,320 7/1992 Hahn et al. ..... 514/12
5,565,428 10/1996 Clark et al. ..... 514/12

*Primary Examiner*—Peter A. Nelson
*Attorney, Agent, or Firm*—Woodcock Washburn Kurtz Mackiewicz & Norris LLP; Doreen Yatko Trujillo

[57] ABSTRACT

A method for determining a concentration of IGF-I that defines a therapeutically effective dose of IGF-I, i.e., a dose that will provide a therapeutic response in the treatment of neurological disorders for which IGF-I is utilized (including peripheral neuropathy, diabetic neuropathy, post-polio syndrome, small fiber neuropathy, ALS, and MS) is described. The method comprises determining whether a particular dose of IGF-I causes a 1.5 fold or greater increase in the homeostatic concentration of plasma IGFBP-2 in a mammal that has previously received a defined dose of IGF-I. The method of the invention can also be used to determine whether or not biological tolerance has developed to a particular dose of IGF-I.

2 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DIAGNOSTIC USES OF IGFBP-2

FIELD OF THE INVENTION

Our invention relates to a method of using an increase in the plasma concentration of IGFBP-2 as an indicator that a therapeutically effective dose of recombinant human insulin-like growth factor-I (IGF-I) has been received by a mammal in the treatment of those disorders for which IGF-I is indicated as being useful. Such disorders include in particular, neurological disorders exemplified by peripheral neuropathy, diabetic neuropathy, post-polio syndrome, small fiber neuropathy, amyotrophic lateral sclerosis (ALS), multiple sclerosis (MS) and with particular emphasis on ALS.

BACKGROUND OF THE INVENTION

Insulin-like growth factor-I (IGF-I) is a 70-amino acid, single-chain peptide and a member of the insulin family of peptides, which also includes insulin and insulin like growth factors II (IGF-II ) and III (IGF-III). IGF-I plays an essential role in growth and development of many tissues (Liu et al., *Cell :* 59–72, 1993; Baker et al., *Cell* 75: 73–82, 1993). In the central nervous system, IGF-I is expressed during fetal development of the brain and peripheral nerves (Werner et al., *Proc. Natl. Acad. Sci. USA* 86: 7451–7455, 1989; de Pablo et al.,*TINS* 18: 143–150, 1995). Both in-vitro and in-vivo studies have demonstrated that IGF-I and IGF-II promote motor neuron survival, proliferation and neurite outgrowth (Caroni, P., et al., *J. Cell Biol.,* 110: 1307–1317, 1990). In-vitro studies have shown that IGF-I promotes the survival of astrocytes and neuronal precursor cells from fetal rat brain and motor neurons (Ang et al., *J. Neurol. Sci.* 109: 169–172, 1992; Komoloy et al., *Proc. Nat;. Acad. Sci. USA* 89:1894–1898, 1992; Hughes et al., *J. Neurosci. Res.* 36:663–671, 1993; Gammeltoft et al., pp.295–305, in The Insulin-like Growth Factors and Their Regulatory Proteins, Elsevier Science B.V., Amsterdam, The Netherlands, 1994 editors, Baxter et al.). In-vivo studies have demonstrated that local infusion of IGF-I to the proximal end of a cut sciatic nerve promotes regeneration of the peripheral nerve (Nachemson et. al., *Growth Factors* 3: 9–314, 1990). Furthermore, recent studies demonstrate that repeated (chronic) systemic administration of recombinant human insulin-like growth factor-I (rhIGF-I) to mice enhances the functional recovery of the sciatic nerve following bilateral crush of sciatic nerves (Contreras et al., *J.Pharmacol. and Exp. Therapeut.* 274(3): 1443–1449, 199). Taken together, these studies have suggested that IGF-I has therapeutic value in certain pathological conditions involving motor neurons such as peripheral neuropathies (peripheral neuropathy generally refers to a disorder that affects the peripheral nerves, most often manifested as one or a combination of motor, sensory, sensorimotor, or autonomic neural dysfunction), ALS and other neurological diseases. (Lewis et al.,*Ann. N.Y. Acad. Sci.* 692: 201–208, 1993. See also, U.S. Pat. No. 5,093,317 and U.S. Pat. No. 5,420,112). Pre-clinical studies have also shown that IGF-I promotes neuronal sprouting (the natural process by which neurons generate additional branches, enabling them to establish functional contacts with muscle fibers whose original nerve contacts have been lost as a result of neuronal death) and function of peripheral nerves, and induces skeletal muscle hypertrophy, or enlargement of muscle cells, in the presence of neurodegenerative conditions.

U.S. Pat. No. 5,420,112 discloses the use of IGF-I to treat peripheral nerve damage, called peripheral neuropathy, caused by peripheral-neuropathy-causing toxic agents. ALS is a fatal neuromuscular disease characterized by the chronic, progressive degeneration of motor neurons which leads to muscle weakness, muscle atrophy, and eventually death from respiratory failure. U.S. Pat. No. 5,093,317 discloses the use of IGF-I in the treatment of certain disorders such as ALS. Cephalon Inc.'s Phase III clinical studies of MYOTROPHIN® (rhIGF-I) have shown that patients with ALS who received MYOTROPHIN recombinant protein experienced less disease severity, slower progression of disease, and better functional ability compared to patients who received placebo. After nine months of therapy, patients who received 0.10 mg/kg per day of MYOTROPHIN recombinant protein showed approximately 25 percent less deterioration than patients receiving placebo. The data demonstrate statistically significant effects of MYOTROPHIN recombinant protein on ALS disease severity and progression. The data also suggest that the effects of MYOTROPHIN recombinant protein administration are dose-dependent. In these studies, continuous, daily, injection of IGF-I for the life of the patient is contemplated.

While the results of the cited clinical trials establish that administration of IGF-I deters the effects of neurological diseases, such as ALS, there is no rapid, immediate method to determine whether a patient is receiving a therapeutically effective dose of IGF-I for the treatment of the disease or condition being treated. Determining an effective per patient dose of IGF-I is important for a beneficial therapeutic regimen, as a patient may not reap the complete benefits of the administered drug if a less than effective dose is administered. Furthermore, a beneficial therapeutic outcome may not result if a dose of IGF-I that is chronically administered results in biochemical tolerance. Ideally, it would be beneficial to both a physician and a patient receiving IGF-I if a Surrogate Biochemical Marker (SBM) within the patient could be assessed to determine if an effective dose of the therapeutic has been administered.

An SBM is a measure of some parameter associated with, but not a direct measure of, drug efficacy. Whereas physiologic markers (endpoint measurements, such as disease episodes, quality of life measures, mortality, etc.) do not always provide the level of accuracy and precision required to detect small changes and thus make resulting data of limited value, SBMs can provide a specific and graded quantitative measurement of a drug's effect on the body's response within a short time. Thus, SBMs can be useful for determining the appropriate dose regimen for each particular patient and as an aid in ensuring that the patient is receiving a therapeutically effective dose of a therapeutic drug such as IGF-I. For a review on SBMs, see Lee et al., *J. Clin. Pharmacol.* 464–470, 1995.

In response to either an initial (acute) or repeated (chronic) administration of rhIGF-I, plasma glucose concentrations decrease. This is consistent with previous reports which show that IGF-I has insulin-like activity on blood glucose concentrations (Snyder et al., *J. Clin. Endocrinol. Ans Metab.* 71: 1632–1636, 1990; for review see Froesh et al., *Ann. Rev. Physiol.* 47: 443–467, 1985). Thus, plasma glucose might be considered a possible SBM. However, changes in plasma glucose concentrations are not useful as a SBM for determining whether a patient has been given a therapeutically effective dose of IGF-I because several other factors, including circadian rhythms, nutrition, activity and stress levels also effect plasma glucose concentrations.

High affinity insulin-like growth factor binding proteins (IGFPBs) are important modulators of cellular responsiveness to IGF-I. (Clemmons, *Growth Regulation,* 2: 80–87, 1992). Insulin-like growth factor binding proteins (IGFBPs)

are thought to facilitate transport of IGF-I, to modulate the actions of IGF-I on target cells and to control IGF transport in blood and out of the vascular compartment, localizing and modulating IGFs to specific cell types and binding to receptors and regulating blood glucose levels. (Lewitt et al.,*Mol. Cell Endocrinol.* 79: 147–152, 1991; Lewitt et al., *Endocrin.* 129: 2254–2256, 1991, Holly, *Acta Endocrinol.* 124: 55–62 1991; for review see Clemmons, *Mol. Reprod. and Develop.* 35: 368–375, 1993). While 95% of plasma IGF-I is associated with binding with IGFBP-3, the remaining 5% of IGF-I has been shown to be bound to IGFBP-1, -2, and -4. A study in transgenic mice that over expressed the IGF-I gene led the authors to conclude that those mice have greater levels of IGFBP-2 and IGFBP-3, and that IGF-I is a major controller of these binding proteins (Camacho-Hubner et al., *Endocrinology* 129: 1201–1206, 1991). Another study by Clemmons et al., (*J. Clin Endocrinol Metab.* 727–733, 1991) determined the nutritional and hormonal variables that regulate IGFBP-2 in humans, reporting that plasma IGFBP-2 levels were not suppressed in acromegaly, post prandially, after administration of growth hormone, acute stimulation of insulin secretion or after glucose infusion. Extreme insulin deficiency, however, resulted in a 1.7 fold increase in IGFBP-2.

The IGFBPs in mammalian plasma range between 24 kDa and 55 kDa with respect to their molecular weights. IGFBP-3 appears as a doublet (48–55 kDa) presumably due to different glycosylation states; IGFBP-2 is a 34–36 kDa protein; IGFBP-1 has a molecular mass ($M_r$) of 31 kDa and IGFBP-4 appears at 24 kDa (Camacho-Hubner et al., 1991, supra).

IGF-I is highly conserved across mammalian species. For example, there are only minor differences between the amino acid sequences of rat and human IGF-I. The observed differences between rat and human IGF-I are relatively few and mostly conserved in nature; there are no differences between bovine, porcine, and human IGF-I (Daughaday et al., *Endocrine Rev.,* 10(1):68–91, 1989). As such, and beneficially, those in the art have utilized recombinant human IGF-I (rhIGF-I) for in vivo investigations in animal models, including mice and rats, indicating the highly conserved nature of the protein and its receptor.

SUMMARY OF THE INVENTION

We disclose a method for determining whether a dose of IGF-I which mammals are receiving is an appropriate and therapeutically effective dose for the treatment of disorders for which IGF-I is utilized. Neurological disorders are particularly highlighted in this context. We further disclose a method for assessing whether a mammal has become tolerant to a therapeutically effective dose of IGF-I which has been repeatedly administered for treatment of disorders for which IGF-I is utilized. Again, neurological disorders are particularly highlighted in this context.

In its most preferred embodiment, the method comprises the step of determining a patient's plasma concentration of IGFBP-2 (homeostatic IGFBP-2 concentration) prior to daily administration of a defined dose of IGF-I. The defined dose is given for a period of at least 7 days, preferably for at least 17 days. After completion of the treatment regimen, the plasma concentration of IGFBP-2 between 0.5 and 10 hours, preferably 3 hours, after the IGF-I is last administered is determined (post-treatment IGFBP-2 concentration) and compared with the patient's homeostatic IGFBP-2 concentration. At least a 1.5 fold or greater increase in the post-treatment IGFBP-2 concentration relative to the homeostatic IGFBP-2 concentration indicates that a therapeutically effective dose of IGF-I has been administered. After continuous daily administration of IGF-I for a period in excess of 17 days, IGFB-2 concentration can be further determined (also referred to as post-treatment concentration), where less than a 1.5 fold increase in the post-treatment IGFBP-2 concentration relative to the homeostatic IGFBP-2 concentration indicates that the dose being given is not the optimal, therapeutically effective dose for that patient. The method also permits determining if the patient has become tolerant to a particular dose of IGF-I.

Less than a 1.5 fold, or greater, increase as measured above indicates that the mammal has become tolerant to that dose of IGF-I and that the dose may no longer be a therapeutically effective dose. In both cases, this allows a physician to consider alternative dosing levels of IGF-I.

BRIEF DESCRIPTION OF THE FIGURES AND THE DRAWINGS

DETAILED DESCRIPTION

For purposes of this invention, the phrase "therapeutically effective dose" means the dose of IGF-I that enhances the rate of functional recovery or slows the rate of functional loss of whatever neurological condition is being treated.

For purposes of this invention, the phrase "to be tested" in reference to a dose of IGF-I means a dose of IGF-I that is presumed to be a therapeutically effective dose.

For purposes of this invention, the phrase "final dose" in reference to a dose of IGF-I means the dose of IGF-I provided to a mammal immediately prior to determination of post-treatment IGFBP-2 concentration.

As used herein, the phrase "about" means ± about 10% of the value modified thereby.

Evidence suggests that IGF-I plays a key role in nerve regeneration and sprouting (Henderson et al., *Nature* 302: 609–611, 1983; Near et al., *Proc. Natl. Acad. Sci* 89: 11716–11720, 1992; Gehrmann et al., *Exp. Neurol.* 128: 1–9, 1994; Caroni et al., supra, 1994; Contreras et al., supra, 1995,). It has further been shown that systemic administration of rhIGF-I enhances the rate of functional recovery of injured sciatic nerves of adult mice (Contreras et al., supra, 1995). The results of the Contreras et al., study show that a bell-shaped dose-response curve exists for rhIGF-I and that the optimum therapeutically effective dose for enhancing functional recovery in injured sciatic nerves of mice is about 1 mg/kg of rhIGF-I.

To find a biochemical marker with a reliable physiological response to the administration of IGF-I, to possibly serve as a SBM, the plasma concentrations of osteocalcin, IGFBP-2, IGFBP-3, IGFBP-4, glucose and Type-I IGF receptor density were determined following the administration of a therapeutically effective dose of rhIGF-I (1 mg/kg) to mice (Contreras et al., supra). Only glucose and IGFBP-2 showed significant and reliable changes from their respective homeostatic concentrations. Because many factors are known to affect the concentration of glucose, the response of IGFBP-2 was investigated as a potential SBM.

Figure 3:
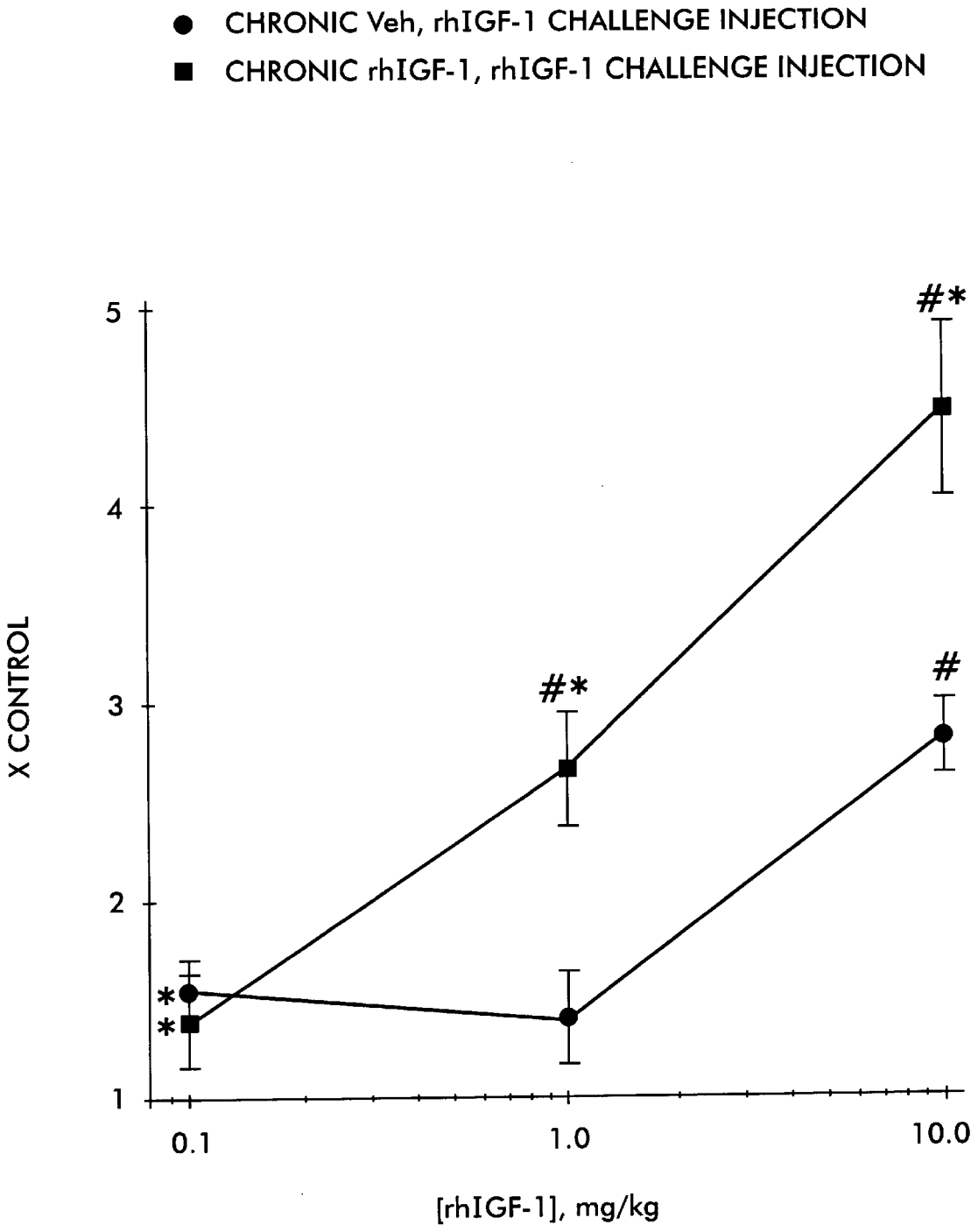
FIG. 3 shows the plasma concentrations in mice of IGFBPs determined at 3 hours after receiving 0.1, 1.0 or 10.0 mg/kg rhIGF-I.

We have determined that IGFBP-2 is an effective SBM for assessing therapeutically effective IGF-I responses in mammals. We have discovered that those doses of IGF-I which are therapeutically effective cause an increase of 1.5 fold or greater in the plasma concentration of IGFBP-2 (FIG. 3). Therefore, a method comprising determining the concentration of IGF-I that reliably causes a 1.5 fold or greater increase in the plasma concentration of IGFBP-2 in a mammal is a useful method for determining a therapeutically effective dose of IGF-I in that mammal. Furthermore, the presence or absence of a 1.5 fold or greater increase in the plasma concentration of IGFBP-2 in a mammal after repeated administrations of a previously determined therapeutically effective dose of IGF-I permits the assessment of whether or not physiological tolerance to that dose has occurred. Disclosed is an example that the administration of a therapeutically effective dose of IGF-I to a mammal for up to 17 days did not result in biochemical tolerance. This is important because therapeutic treatment of neurological disorders using IGF-I requires a regime of long term daily administration. The method is applicable to any mammals for which it is desired to treat neurological pathologies by the administration of IGF-I.

Having described our discovery in broad terms above, the data below will provide specific data which exemplify the invention. The examples are for purposes of illustration and are not intended to be limiting of the invention or any embodiment of it.

I. GENERAL METHODS a. Experimental Animals and Protocol

Male CD-1 mice (Charles River, Raleigh, N.C.) between 45–60 days of age were used in the acute (Ac) studies (i.e., mice receiving a single injection of either rhIGF-I or vehicle) and the chronic (Chr) studies (i.e., mice receiving multiple daily injections of either rhIGF-I or vehicle). All mice were housed with five mice per cage, maintained on a 12 hour light/dark cycle and allowed access to food and water ad libitum.

All mice were dosed with rhIGF-I (98% purity; Cephalon, West Chester, Pa.) or vehicle (0.1M sodium acetate pH 4.0) at the same time of day (between 10.00–11.00 a.m.). After either single (Ac) or multiple (Chr) subcutaneous (s.c.) injections (0.2 c.c., prepared daily from an 8 mg/ml stock of rhIGF-I solution) of rhIGF-I, mice were anesthetized with $CO_2$ and blood was obtained via intracardiac puncture. Blood samples were immediately introduced into MICROTAINER™ heparinized tubes (Becton Dickinson, Rutherford, N.J.) and kept on ice for 10 minutes. Samples were centrifuged for 10 minutes at 20,000×g in a table top Eppendorf centrifuge. Plasma (the supernatant fluid) was removed and frozen at −80° C. until use.

b. Determination of Plasma Glucose Concentrations

Glucose concentrations were assessed in plasma using a glucose assay kit (SIGMA Diagnostics; St. Louis, Mo.). Briefly, 10 μl of plasma (in duplicate) or glucose standards (provided in kit) were incubated with 1 ml of glucose assay reagent for 10 minutes at room temperature. The reaction was terminated by the addition of 10 ml of 0.1N hydrochloric acid. Samples were transferred to cuvettes and the absorbance (Abs) was determined in a spectrophotometer at 520 nm.

c. Determination of the Plasma Concentrations of IGFBPs

IGFBPs were analyzed from plasma samples using a modified Western/ligand blot method (Hossenlopp et. al., *Anal. Biochem.* 154: 138–143, 1986; Fazleabas et al., *Anal. Biochem.* 202: 40–45, 1992). Ten μl of 3× Laemelli sample buffer (Laemelli, *Nature* 227: 680–685, 1970), [2% sodium dodecyl sulfate (SDS), 125 mM Tris-HCl, 10% (w/v) glycerol] was added to each 20 μl sample of plasma and 2 μl of bromophenol blue. Samples were then diluted 1:4 with 1 × sample buffer and boiled for 5 minutes. Proteins were electrophoresed on a 12% SDS-polyacrylamide gel at 75V for 3h and then transferred to nitrocellulose membranes overnight in transfer buffer containing 0.125 mM ethanolamine (pH 9.5). Blots were washed in 125 mM Tris buffered saline (TBS), pH 7.4 for 30 minutes at room temperature followed by a 2h incubation with TBS containing 1% bovine serum albumin (BSA). Blots were then incubated with 50 pM (3-[$^{125}$I]iodotyrosyl) IGF-I; [specific activity 2000 Ci/mmol (Amersham, UK)] in TBS containing 1% BSA and 0.1% Tween-20 for 48 hours. Blots were washed three times (15 minutes for each wash) with TBS containing 0.1% Tween-20 followed by 2 washes in TBS. Blots were air-dried, placed in a Phosphor-Imager cassette and exposed for one day.

To determine whether an increase in protein and ligand results in a corresponding increase in binding, plasma samples containing 0.58, 2.93, 5.87, 11.7 and 23.4 μg protein were loaded on each SDS-PAGE gel (n=6). Following transfer onto nitrocellulose membranes, each blot was probed with either 7.81 pM, 15.625 pM, 31.25 pM, 62.5 pM, 125 pM or 250 pM [$^{125}$I]IGF-I. Blots were placed in cassettes and scanned using the Phosphor Imager (Molecular Dynamics, Ca, Model #400 and the Image Quant Computer Program from the same company). The densitometric values (volume) from the Phosphor Imager i.e, 1 μl spots on the nitrocellulose membrane were first correlated with actual amounts of radioactivity (dpm) by counting aliquots directly in the gamma counter. Correlation between the densitometric units and dpm was determined ($r^2$=0.99). Based on this, quantitation, bands from each blot in densitometric units (volume) were converted into dpms and then into fmoles of [$^{125}$I]IGF-I. Further characterization of the Western/ligand blot method for IGFBPs revealed a linear relationship between increasing protein concentration (0.58 –23.4 μg) and fmoles bound for IGFBP-2, IGFBP-3 and IGFBP-4. The optimal protein concentration and concentration of [$^{125}$I] IGF-I to visualize changes in binding to the IGFBPs following acute or chronic treatment were found to be 5–10 μg and 31.25–62.5 pM, respectively.

The molecular weights of the IGFBPs in plasma range between 24 kDa and 55 kDa. IGFBP-1 has a molecular mass ($M_r$) of 31 kDa; IGFBP-2 is a 34–36 kDa protein; IGFBP-3 appears as a 48–55 kDa doublet presumably due to different glycosylation states, and IGFBP-4 appears as a 24 kDa protein (Camacho-Hubner et al., 1991; Clemmons et al., 1993). IGFBPs corresponding to IGFBP-2, IGFBP-3 and IGFBP-4 were visualized after Western/ligand blot analysis. The incubation of a second, duplicate nitrocellulose blot with a 1000 fold excess of non-radioactive IGF-I prior to the addition of radioactive IGF-I prevented specific binding of [$^{125}$I]IGF-I to the IGFBPs (data not shown), thus verifying the identity of the blots. The addition of high concentrations of IGF-I to mouse plasma samples did not alter the density of the IGFBP bands suggesting that endogenous amounts of IGF-I are not carried along with IGFBPs during gel electrophoresis (data not shown).

d. Data Analysis

Data were analyzed using a 2-way Analysis of Variance (ANOVA). When significant effects of treatment were observed, data were further analyzed by Duncan's Multiple Range test. These statistical tests determine and define when a significant increase in the plasma concentration of IGFBP-2 is found.

II. EXAMPLES

Example 1: Reduced Concentration of Plasma Glucose After 17 Daily Administrations of rhIGF-I.

A group of 24 mice were injected daily for 16 days with what has been previously determined to be a therapeutically effective dose of rhIGF-I for mice in the sciatic crush model, i.e., 1 mg/kg. Another group of 30 control mice were similarly injected but with vehicle only. On day 17, 24 control and 24 treated mice were injected with 1 mg/kg of rhIGF-I and blood samples were taken from 6 control mice just before injection and from 6 mice of both groups at 0.5, 3, 6, and 24 hours after receiving the injections. Glucose concentrations were assessed in the plasma samples as described above. The concentration at each time thus represents the average of the concentrations of samples from 6 mice.

It was determined that the plasma glucose concentrations were reduced in both groups of mice (i.e., those receiving either rhIGF-I or vehicle ) by about 30% with the time at which maximal reductions occurred being about 0.5 hour. Thus, mice which had not previously received any rhIGF-I, as well as mice which had received 1 mg/kg of rhIGF-I (a therapeutically effective dose), daily for 17 days, had similar glucose responses. The plasma glucose concentrations of both groups of mice were significantly reduced. The observed decreases in plasma glucose concentrations in response to IGF-I administration is consistent with previous reports which show that IGF-I has insulin-like activity and reduces blood glucose concentrations (Zapf et al., *J. Clin. Invest* 77: 1768–1775, 1986; Snyder et al., *J. Clin. Endocrinol. Ans Metab.* 71: 1632–1636, 1990; for review see Froesh et al., *Ann. Rev. Physiol.* 47: 443–467, 1985). This experiment also shows that repeated administrations of rhIGF-I did not result in biochemical tolerance to the hypoglycemic response to a further dose of rhIGF-I. Neither an increased response nor tolerance to the peak hypoglycemic effects of IGF-I were observed. As previously noted, circadian rhythms, nutrition and stress can also affect plasma glucose levels. Thus, under our criteria, plasma glucose levels would not be an appropriate SBM.

Example 2: Determination of the Responses of Plasma Concentrations of IGFBPs After 17 Daily Administrations of rhIGF-I In this example, we disclose that IGFBP-2 levels are increased by at least 1.5 fold following administration of a therapeutically effective dose of rhIGF-I for at least 7 and, preferably, at least 17 days.

Figure 1:
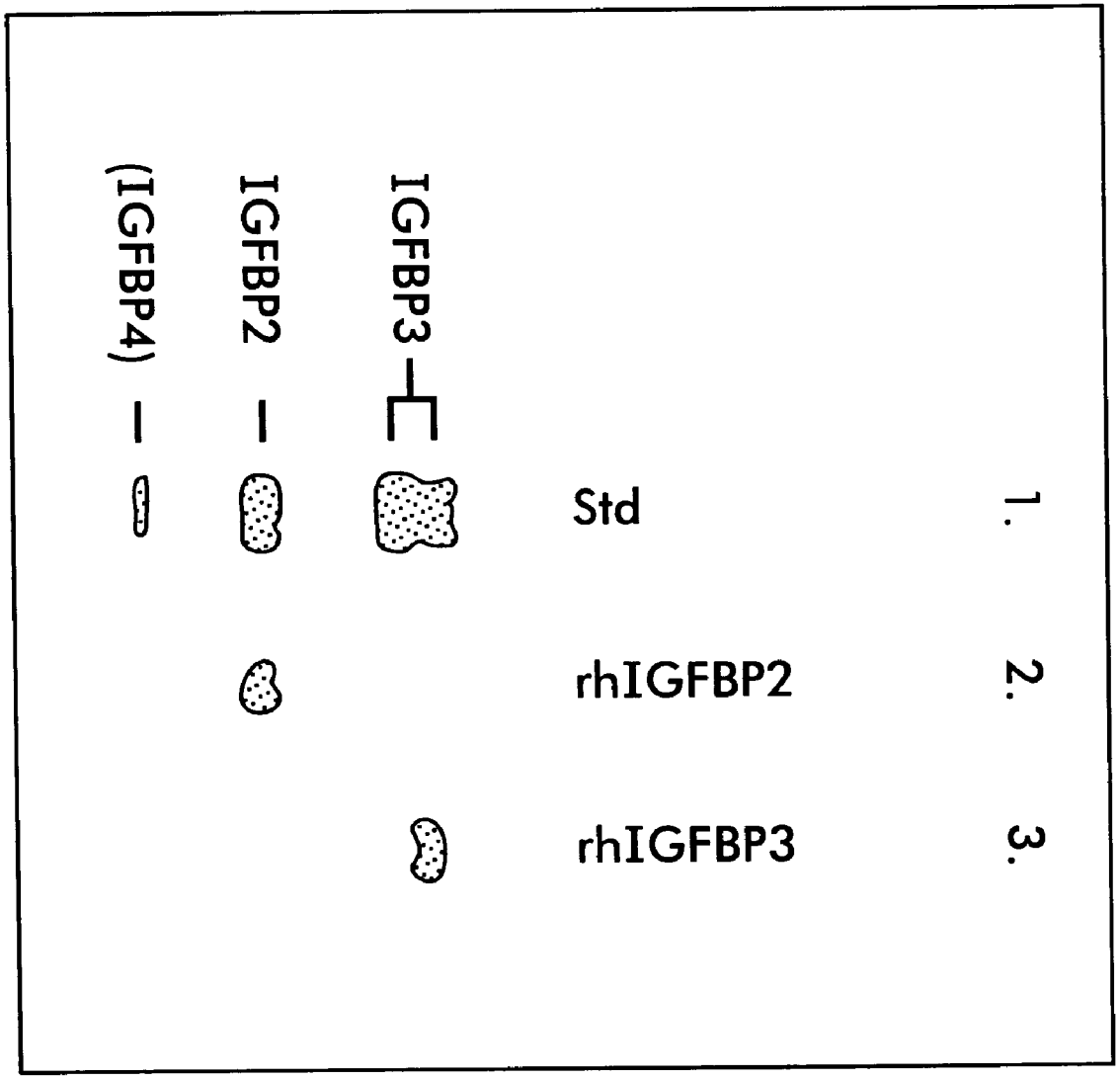
FIG. 1 shows the Western ligand Blot identification of IGFBPs -2, -3, and -4 in plasma from mice prior to the administration of 1 mg/kg of rhIGF-I.

Seven $\mu$g of protein from plasma from mice prior to administration of rhIGF-I was electophoresed, transferred onto nitrocellulose blots and incubated with 50 pM [$^{125}$I] IGF-I as described under "General Methods". Following analysis of the resulting Western / ligand blots, three major bands were visualized. (FIG. 1, lane 1) The 48–55 kDa doublet band reflects IGFBP-3; the 34 kDa singlet band reflects IGFBP-2. The estimated molecular weights was determined by comparison with defined standards of known molecular weights (not shown) and are consistent with previous published reports (Camacho-Hubner et al., 1991, supra; Clemmons et al., 1993, supra). The identity of IGFBP-2 and IGFBP-3 was further confirmed by comparing the bands with those of purified rhIGFBP-2 and rhIGFBP-3 (lanes 2 and 3, respectively, FIG. 1). The 24 kDa (lane 1, FIG. 1) band has been previously reported to be IGFBP-4 (Camacho-Hubner et al., 1991; supra, Clemmons et al., 1993, supra). Due to the unavailability of purified rhIGFBP-4, direct identity comparisons could not be made. We assume that the 24 kDa band represents IGFBP-4. In some of the experiments, a faint band at ~31 kDa (presumably IGFBP-1) was also observed. Densitometric analyses using a Phosphor Imager revealed that the values for these faint bands were near background levels and could not be measured reliably. Therefore, further characterization and quantitation of IGFBP-2, IGFBP-3, and IGFBP-4 were carried out.

Figure 2:
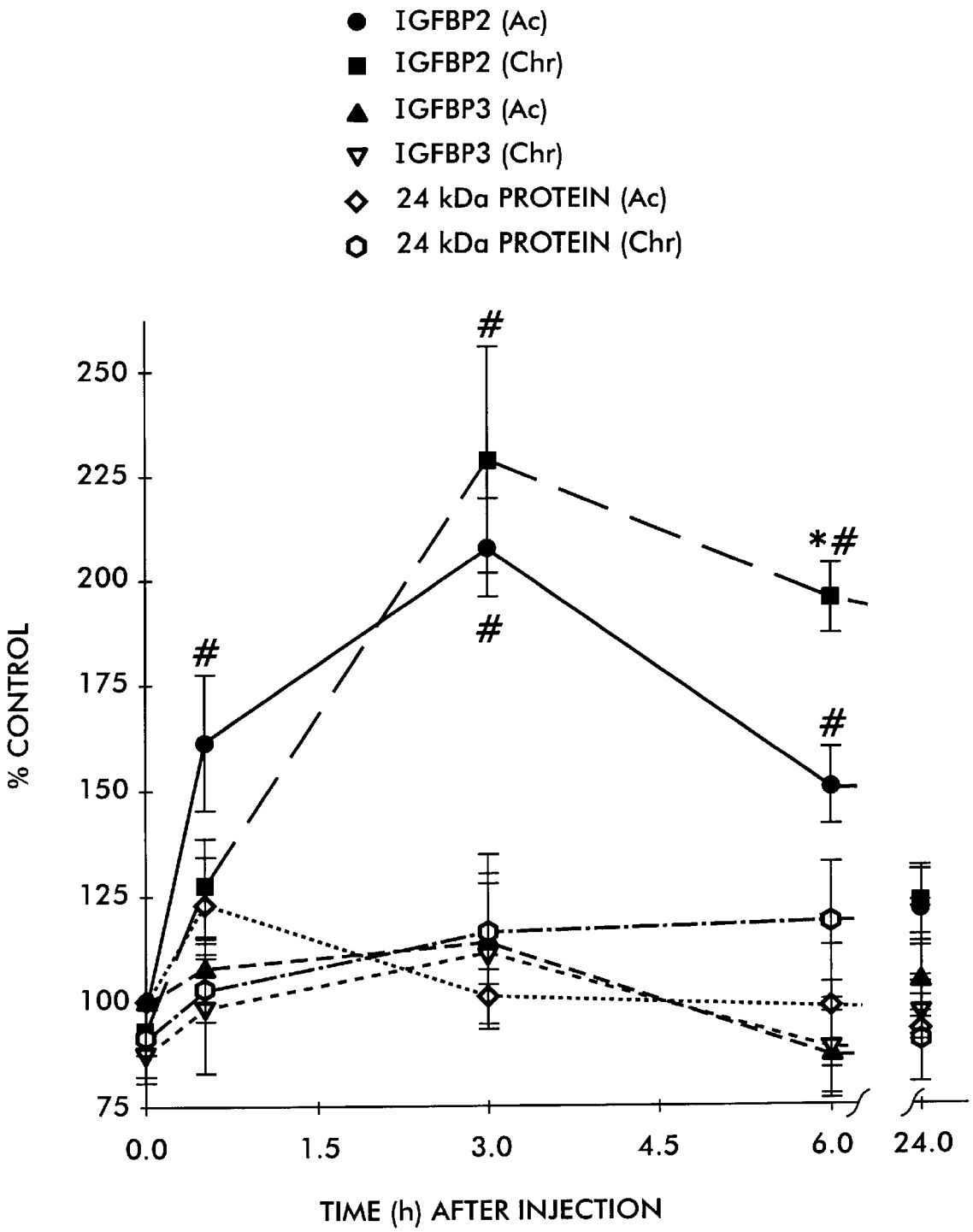
FIG. 2 shows the plasma concentrations of IGFBPs 2, 3 and 4 in mice at various times after the administration of 1 mg/kg of rhIGF-I.

Two groups of 30 mice were used to determine whether there was a response to rhIGF-I and, if so, the time course of the response of the three IGFBPs—IGFBP-2, IGFBP-3, and IGFBP-4. One group of mice received injections of 1 mg/kg of rhIGF-I for 16 consecutive days (Chr). The other group of mice received injections of vehicle for 16 consecutive days (Ac). On day 17, both groups of mice received an injection of 1 mg/kg of rhIGF-I. Plasma was collected from 6 mice just prior to the injection of the 1 mg/kg of rhIGF-I and 6 mice from each of the control and treated groups at 0.5, 3, 6, and 24 hours after the injection of the rhIGF-I. The results are shown in FIG. 2. Of the three IGFBPs, IGFBP-2 evidenced a 1.5 fold or greater increase in its plasma concentration and that higher concentration was present in the plasma at 1 hour after receipt of the initial dose of rhIGF-I (Ac), and 3 hours after the receipt of the 17th dose (Chr). The increased concentrations of IGFBP-2 remained at concentrations above 1.5 fold that of the starting level until about 6 hours but less than 24 hours hour after receipt of the rhIGF-I. No significant changes in the plasma concentrations of IGFBP-3 and IGFBP-4 were found. In FIG. 2 and the figures which follow, an "*" indicates that the values shown are statistically significant relative to the control values. The "#" symbol indicates that there is a statistically significant difference between the two values.

Example 3: Correlation Between the Increase of Plasma

Concentrations of IGFBP-2 and Dose of rhIGF-I

In this experiment, we confirmed the relationship of the 1.5 fold or greater increase in IGFBP-2 concentration in response to the administration of IGF-I to the therapeutically effective dose of IGF-I. As noted previously, for mice in the sciatic crush model, a therapeutically effective dose is 1.0 mg/kg of rhIGF-I. Mice were prepared for this experiment essentially as in Example 2. Each of 3 groups of 6 mice each received injections of either 0.1, 1.0, or 10.0 mg/kg of rhIGF-I for 16 consecutive days (Chr). Another group of 24 mice received injections of vehicle for 16 consecutive days (Ac). On day 17, the mice which had received 0.1 mg/kg of rhIGF-I for 16 days received a 17th injection of 0.1 mg/kg of rhIGF-I. The mice which had received 1.0 mg/kg of rhIGF-I for 16 days received a 17th injection of 1.0 mg/kg of rhIGF-I and mice which had received 10.0 mg/kg of IGF-I for 16 days received a 17$^{th}$ injection of 10.0 mg/kg of rhIGF-I. One group of 6 mice which had received vehicle for 16 days was bled prior to receiving any rhIGF-I to provide the homeostatic or control value of IGFBP-2. Three other groups of 6 mice which had received vehicle for 16 days received an additional dose consisting of either 0.1, 1.0 or 10 mg/kg of IGF-I on day 17. The plasma concentrations of IGFBP-2, were determined in samples of plasma collected at 3 hours after the administration of the last doses of IGF-I. This time was used because it was the time when the maximal increase in the concentration was found (FIG. 2).

The results are shown in FIG. 3. Following an injection of 1 mg/kg or 10 mg/kg, but not 0.1 mg/kg, of rhIGF-I, the plasma concentration of IGFBP-2 increased greater than 1.5 fold only in the group of mice which had received 17 daily administrations of rhIGF-I. The initial administration of rhIGF-I at a concentration of 1 mg/kg sometimes, but not reproducibly, results in a subsequent 1.5 fold increase of IGFBP-2. Mice which had received 17 daily injections of IGF-I had significantly elevated concentrations (two-fold) of plasma IGFBP-2. The increases in IGFBP-2 concentrations in response to an injection of rhIGF-I was found to be dose dependent. The 0.1 mg/kg dose of rhIGF-I failed to alter the plasma concentrations of IGFBP-2 by 1.5 fold. The mice which had received 16 previous 1.0 mg/kg injections of IGF-I and which received the 1.0 mg/kg 17th injection of rhIGF-I showed a 2.7 fold increase in their IGFBP-2 plasma concentrations. The 10 mg/kg initial injection of rhIGF-I caused an increase of 2.7 fold in the IGFBP-2 plasma concentrations in mice which had not received IGF-I previously, and a 4.4 fold increase in the IGFBP-2 plasma concentrations in mice which had received rhIGF-I previously. Furthermore, biochemical tolerance of rhIGF-I was not observed following chronic treatment. A 1.5 fold or greater increase in IGFBP-2 was seen in all mice which had received 16 injections of rhIGF-I at concentrations of 1.0 mg/kg or greater.

IGFBP-2 is not affected by circadian rhythms or glucose levels. IGFBP-2 remains constant throughout the day. Clemmons, *Mol. Reprod. and Devel.,* supra. Clemmons, *J. Clin. Endocrinol. & Metab.* 73: 722–733, 1991, discloses that IGFBP-2 remains stable or increased during normal postprandial changes in insulin and glucose concentrations. Thus acute fluctuations in glucose transport and insulin concentrations within the physiological range have no role in regulating IGFBP-2. Thus the plasma IGFBP-2 levels are not acutely regulated by insulin or glucose. (Clemmons et al., supra 1991). It is important that a marker remain independent of fluctuations is glucose levels so that meals will not effect values. Based on the forgoing, IGFBP-2 can be utilized as an SBM for rhIGF-I.

Example 4: Comparison of the Effects of Insulin and rhIGF-I After Sciatic Nerve Crush We have previously shown that a therapeutically effective dose of rhIGF-I (1.0 mg/kg) decreases plasma glucose, and increases IGFBP-2 by a factor of 1.5 or greater. In order to examine the specificity of the IGFBP-2 response correlated with the therapeutic effectiveness of IGF-I, we have determined whether insulin, which also decreases plasma glucose, similarly increases the plasma concentration of IGFBP-2 and similarly enhances the therapeutic effectiveness on grip after sciatic nerve injury .

Figure 4:
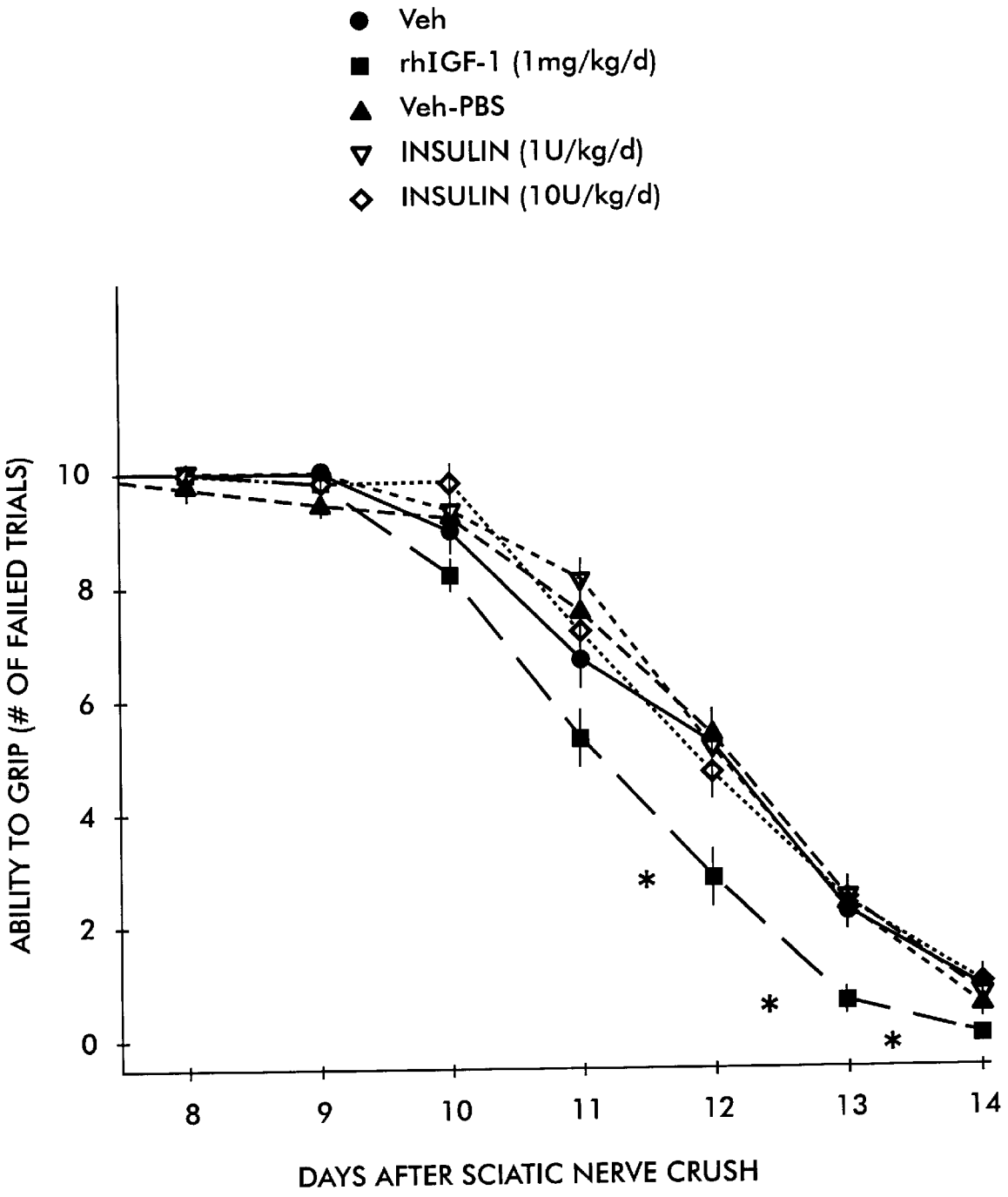
FIG. 4 shows the gripping ability of mice, which have had their sciatic nerves partially crushed.
Figure 5:
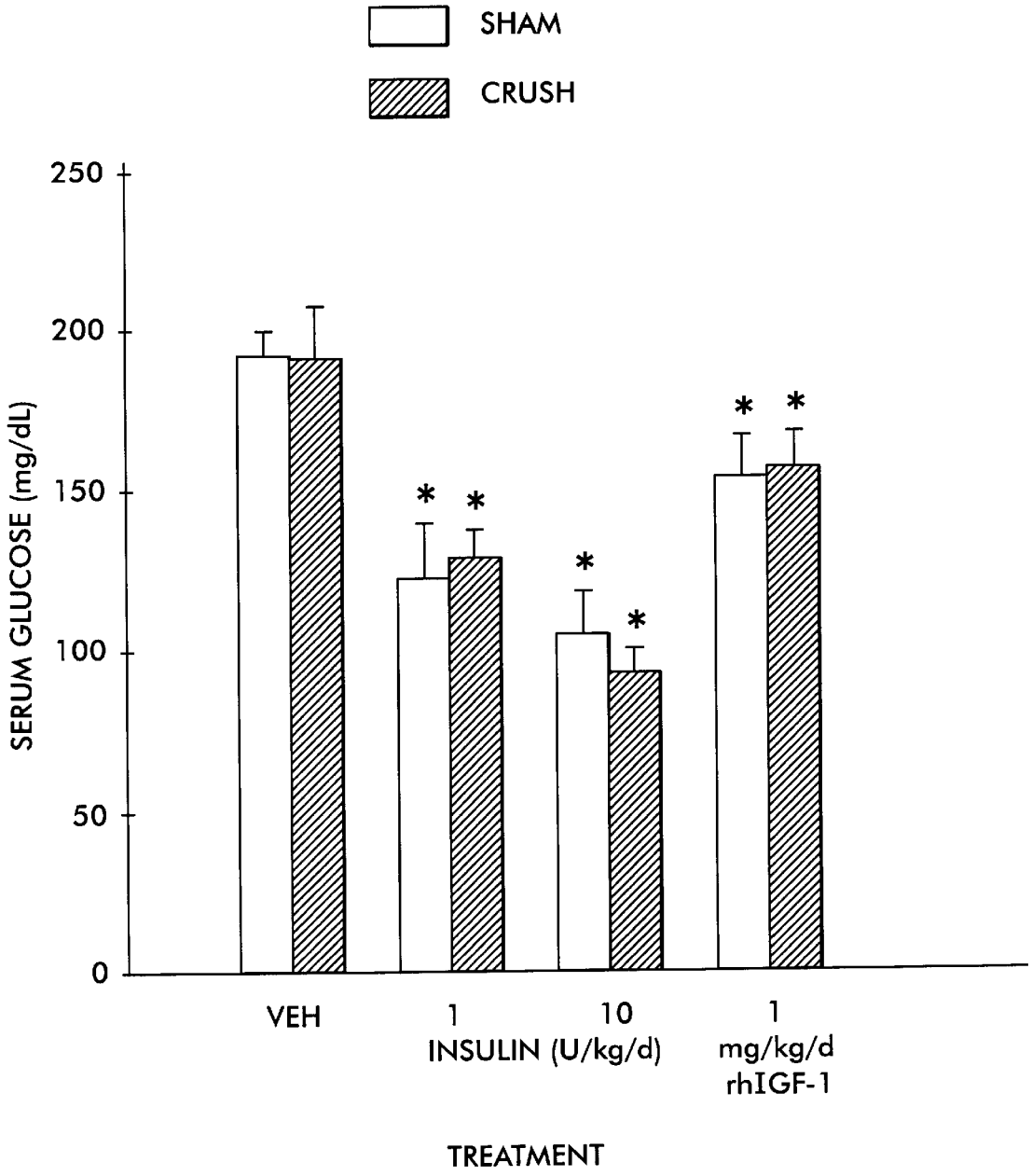
FIG. 5 shows the effects of insulin and rhIGF-I on the concentrations of plasma glucose at 0.5 hour after administration.
Figure 6:
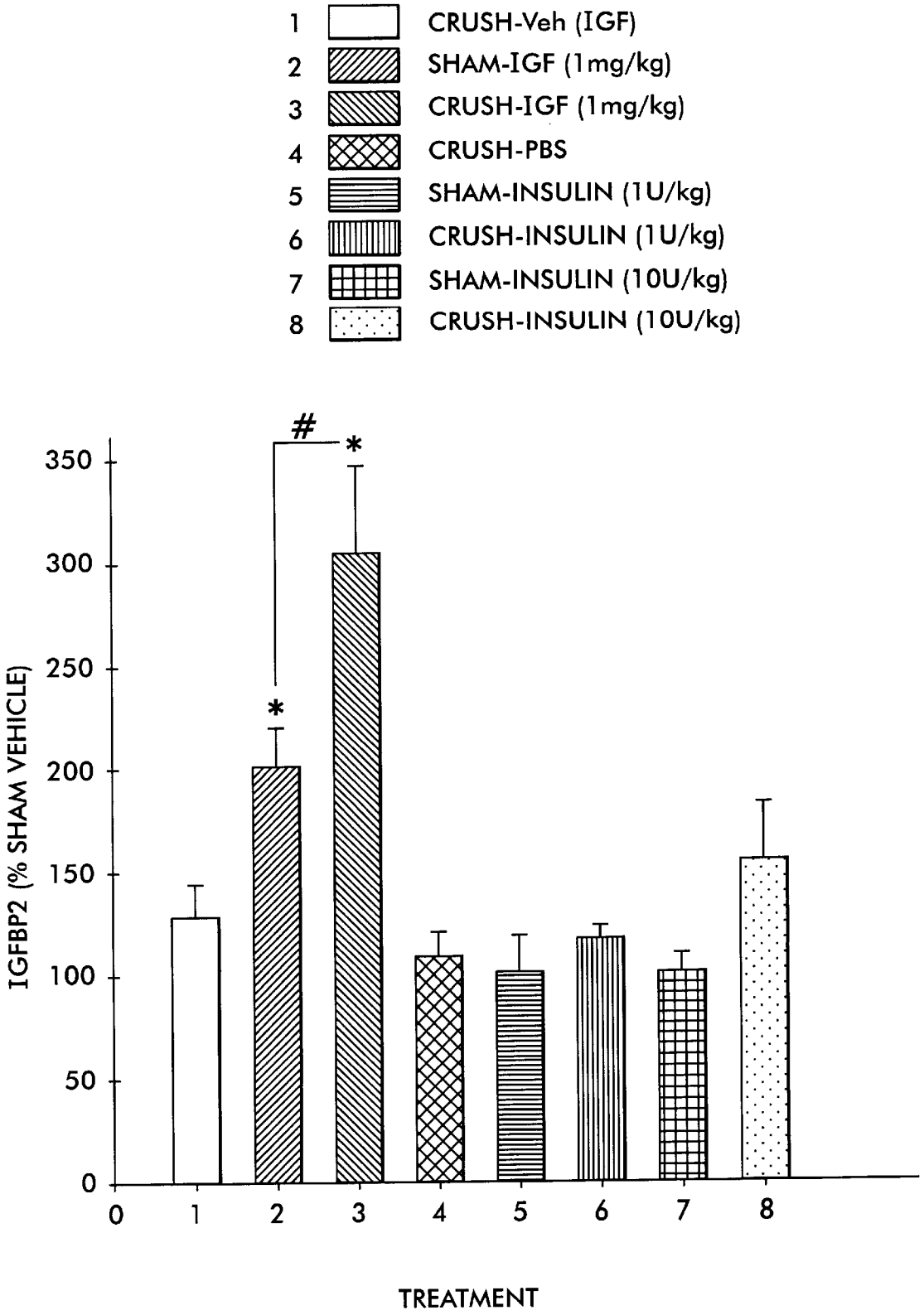
FIG. 6 shows the effects of insulin and rhIGF-I on the concentrations of plasma IGFBP-2 concentrations at 3 hours after administration.

Initially, the time course and dose-response effects of insulin on plasma glucose levels were determined (data not shown). We determined that 1 U/kg and 10 U/kg of insulin caused a similar decrease in plasma glucose to that of a dose of 1 mg/kg of rhIGF-I. In order to compare the effects of multiple injections of insulin and rhIGF-I on behavioral parameters associated with sciatic nerve function and IGFBP-2 levels, 5 groups of 6 CD-1 mice which received bilateral crushes of the sciatic nerves (as per the methods of Contreras et al., supra) were injected daily for 17 days with either vehicle for insulin (phosphate buffered saline, PBS), insulin (1.0, or 10.0 U/kg), vehicle for rhIGF-I or 1 mg/kg of rhIGF-I. All of the mice were then tested daily for their ability to grip an inverted screen (Contreras et al., supra). As shown in FIG. 4, the rate of recovery of grip ability was significantly enhanced after daily injections with 1 mg/kg of rhIGF-I, but not after daily injections of either concentration of insulin. The effects of multiple injections of insulin and rhIGF-I on plasma glucose at 0.5 h after the last injection is shown in FIG. 5. Both agents significantly reduced the concentration of plasma glucose 0.5h after the injection. The reduction caused by 1 U/kg of insulin on plasma glucose was comparable to that caused by 1 mg/kg rhIGF-I. The results shown in FIGS. 4 and 5 indicate that a dose of insulin that reduces the concentration of plasma glucose does not enhance the functional recovery of injured sciatic nerves, and further validates the functional specificity of rhIGF-I. The results depicted in FIG. 6 further show that the administration of rhIGF-I (1 mg/kg) caused greater than 150% increases in the plasma concentrations of IGFBP-2, while either dose (1 mg/kg or 10 mg/kg) of insulin did not. It is clear that the decrease in glucose concentration is not a appropriate marker to predict the therapeutic effects of IGF-I. Furthermore, these results suggest that the enhanced functional recovery effects following repeated administration of 1 mg/kg of rhIGF-I after sciatic nerve crush are mediated through the IGF-I receptor.

In conclusion, the foregoing examples demonstrate that IGFBP-2 can be used as an SBM for IGF-I. Our examples also indicate that the effect of repeated injections of insulin on IGFBP-2, compared with the effect of IGF-I on IGFBP-2, demonstrate that a significant increase in IGFBP-2 was observed after IGF-I injections but not after injections of either 1 U/kg or 10 U/kg of insulin.

All references cited herein are hereby incorporated by reference.

What is claimed is:

1. A method for determining a therapeutically effective dose of IGF-I in a mammal comprising;

a) measuring homeostatic IGFBP-2 concentration in said mammal;

b) administering a dose of IGF-I to be tested to said mammal at least once daily for a period of at least 7 days;

c) administering a final dose of said dose of IGF-I to be tested to said mammal on the day following said period;

d) measuring post-treatment IGFBP-2 in said mammal from at least about 0.5 to at least about 10 hours following said final dose; and e) determining whether post-treatment IGFBP-2 concentration increased 1.5 fold or greater over homeostatic IGFBP-2 concentration for said mammal.

2. A method for screening a mammal receiving a therapeutically effective dose of IGF-I as determined according to claim 1 to determine whether said mammal has become tolerant to said dose of IGF-I comprising;

a) measuring post-treatment IGFBP-2 concentration in said mammal from at least about 0.5 to at least about 10 hours following said therapeutically effective dose of IGF-I; and b) determining whether post-treatment IGFBP-2 concentration increased 1.5 fold or greater over homeostatic IGFBP-2 concentration for said mammal.

* * * * *